(12) United States Patent
Wang

(10) Patent No.: US 6,511,849 B1
(45) Date of Patent: Jan. 28, 2003

(54) MICROARRAYS OF BIOLOGICAL MATERIALS

(75) Inventor: Eugenia Wang, Montreal (CA)

(73) Assignee: The Sir Mortimer B. Davis - Jewish General Hospital, Montreal (CA)

(*) Notice: Subject to any disclaimer, the term of this patent is extended or adjusted under 35 U.S.C. 154(b) by 0 days.

(21) Appl. No.: 09/299,193

(22) Filed: Apr. 23, 1999

(51) Int. Cl.[7] .............................................. G01N 35/02
(52) U.S. Cl. ........................ 436/47; 436/518; 436/501
(58) Field of Search .......................... 436/47, 518, 501; 427/8, 2.13; 435/6, 317.1, 286.3, 286.4, 287.2, 287.3; 417/413.2

(56) References Cited

U.S. PATENT DOCUMENTS

| | | | |
|---|---|---|---|
| 5,474,796 A | 12/1995 | Brennan | 427/2.13 |
| 5,658,802 A | 8/1997 | Hayes et al. | 436/518 |
| 5,744,305 A * | 4/1998 | Fodor et al. | 435/6 |
| 5,837,858 A | 11/1998 | Brennan | 536/25.3 |
| 5,847,105 A | 12/1998 | Baldeschwieler et al. | 536/25.3 |
| 5,985,356 A * | 11/1999 | Schultz et al. | 427/8 |
| 6,001,309 A * | 12/1999 | Gamble et al. | 422/100 |
| 6,245,297 B1 * | 6/2001 | Kowallis | 422/66 |

* cited by examiner

*Primary Examiner*—Jill Warden
*Assistant Examiner*—Brian Sines
(74) *Attorney, Agent, or Firm*—Holland & Knight LLP

(57) ABSTRACT

An apparatus and a method are provided for forming a microarray of biological material on a substrate. The microarrays may consist of nucleic acids, peptides, or the like. The subject invention provides relatively simple and inexpensive machinery to produce the microarrays in a reproducible and rapid manner.

6 Claims, 4 Drawing Sheets

MICROARRAYS OF BIOLOGICAL MATERIALS

FIELD OF THE INVENTION

This invention relates to an apparatus and method for producing microarrays of biological materials.

BACKGROUND OF THE INVENTION

Microarrays of biological materials comprise a support, such as chemically activated paper or glass, on which is arranged a number of small discrete deposits of biological materials such as DNA, RNA, or proteins, in predetermined patterns or arrays. Microarrays can be used for a number of different purposes, including the identification of unknown samples of materials such as DNA and antibodies.

There are two major approaches to the production of microarrays: synthesis and delivery. The synthesis approach involves the production of microarrays in a step-wise fashion by the in situ synthesis of nucleic acids and other biopolymers from biochemical building blocks, such that with each round of synthesis, building blocks are added to growing chains until the desired length is achieved. The delivery approaches, by contrast, use the exogenous deposition of pre-prepared biochemical substances for chip fabrication.

At least three types of technologies are known in the art for automated microarray production. These are photolithography, mechanical microspotting, and ink jet technology. With photolithography, a glass wafer, modified with photolabile protecting groups is selectively activated for DNA synthesis by shining light through a photomask. Repeated deprotection and coupling cycles enable the preparation of high-density oligonucleotide microarrays (see for example, U.S. Pat. No. 5,744,305, issued Apr. 28, 1998).

Microspotting encompasses deposition technologies that enable automated microarray production by printing small quantities of pre-made biochemical substances onto solid surfaces. Printing is accomplished by direct surface contact between the printing substrate and a delivery mechanism, such as a pin or a capillary. Robotic control systems and multiplexed printheads allow automated microarray fabrication.

Ink jet technologies utilize piezoelectric and other forms of propulsion to transfer biochemical substances from miniature nozzles to solid surfaces. Using piezoelectricity, the sample is expelled by passing an electric current through a piezoelectric crystal which expands to expel the sample. Piezoelectric propulsion technologies include continuous and drop-on-demand devices. In addition to piezoelectric ink jets, heat may be used to form and propel drops of fluid using bubble-jet or thermal ink jet heads; however, such thermal ink jets are typically not suitable for the transfer of biological materials due to the heat which is often stressful on biological samples. Examples of the use of ink jet technology include U.S. Pat. No. 5,658,802 (issued Aug. 19, 1997).

The apparatus presently available often suffers from one or more of the following disadvantages: high cost, lack of automatization, sample cross-contamination the requirement for large volumes of sample, and lack of versatility, for instance in the amount and shape of the sample deposited on the microarray. There is, therefore, a need for new methods and apparatus for preparing microarrays. Ideally, such methods should utilize relatively simple and inexpensive machinery to produce the microarrays in a reproducible and rapid manner.

SUMMARY OF THE INVENTION

In one aspect, the invention provides an apparatus for forming a microarray of biological materials on a substrate, comprising: a support adapted to hold the substrate; at least one electro-mechanical fluid ejector, adapted to deliver a sample to the substrate held in said support; a plurality of sample reservoirs; one or more sampling devices, adapted to take up a sample from a sample reservoir; a positioning device for moving the plurality of sample reservoirs and the sampling device relative to each other, so as to position the sampling device adjacent to a selected sample for take up of the selected sample by the sampling device; a conduit for delivering the selected sample taken up in the sampling device to said ejector; and a transport mechanism for moving the substrate-holding support and the ejector relative to each other, such that the mircoarray is produced by delivery of samples to the substrate in a predetermined pattern.

Advantages of the subject invention include the complete automatization of the process, such that samples do not have to be replaced or exchanged during the process. Each sampling device is able to pick up sample from any one of the sample reservoirs and deliver it to an ejector. Thus, a large assortment of samples can be dispensed to form a microarray. Further, computer control can be used, so that no human intervention is required during a run.

Electro-mechanical fluid ejectors (ink jet) are used to deposit small drops of liquid on a solid substrate at rates much more rapid than those achievable with microspotting devices. In addition, such ejectors allow the use of extremely small samples (10 pl to 1 nl). Thus, with an accurate positioning mechanism, microarrays can be formed which have a larger number of probes located within a smaller area than is achievable with many prior methods. The use of extremely small drops also minimizes costs by minimizing the quantity of sample required.

The apparatus itself can be assembled from commercially available components which also make it much more inexpensive than prior art methods which require expensive components manufactured specifically for making microarrays.

In preferred aspects, the invention provides for cleaning of the conduit line through which line the sample is transferred from the sampling device to the ejector, as well as for cleaning and drying of the exterior of the sampling device and the ejector. This provides a means of avoiding contamination, such that a sampling device can be used to pick up and successively deliver any number of different samples to the ejector. This allows for the use of many different samples, again without human intervention being necessary during a run. This also increases the speed at which a microarray can be produced.

In another aspect, the invention provides a commercial package comprising components of the apparatus as described above, together with instructions for the assembly and use of the apparatus.

In a further aspect, the invention provides a method for forming a microarray of biological materials on a substrate, comprising: providing a plurality of sample reservoirs which contain samples; providing a sampling device; positioning the sampling device adjacent to the sample reservoirs; using the sampling device to draw a selected sample into the sampling device from the sample reservoirs; delivering said selected sample to an ejector through a conduit; providing a substrate positioning the ejector adjacent to said substrate; delivering the sample from the ejector to a predetermined location on the substrate; repeating the above steps such that multiple samples are delivered to the substrate at predetermined locations to form a microarray of biological materials.

BRIEF DESCRIPTION OF THE DRAWINGS preferred embodiments of the invention will now be described with reference to the attached drawings in which.

DESCRIPTION OF PREFERRED EMBODIMENTS OF THE INVENTION

Figure 1:
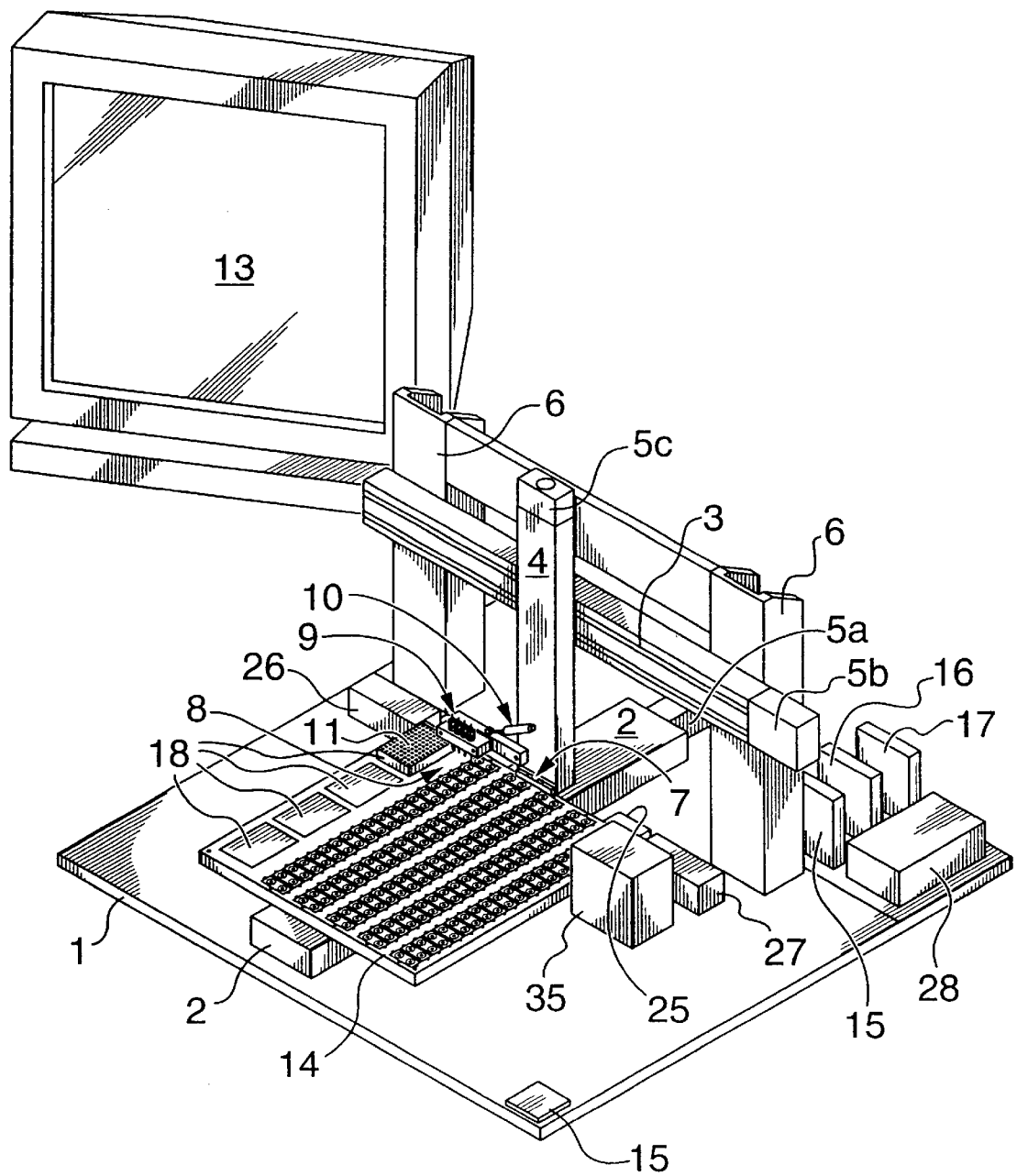
FIG. 1 is a perspective view of an apparatus for forming a microarray of biological materials, in accordance with one embodiment of the invention.

FIGS. 1 to 5 show an apparatus of the invention for forming microarrays of biological materials. As shown FIGS. 1 and 2, the base of the apparatus is a vibration isolation table 1. Mounted on the table 1, by means of a first horizontal linear guide 2, is a platform 14. The platform 14, is connected through a carriage (not shown) to a drive mechanism (not shown) such as a lead screw in the guide 2. The horizontal linear guide 2 carries a computer controlled motor 5a connected to the drive mechanism, which effects movement of the platform 14 back and forth along the first linear guide 2. The motor 5a is linked to a computer 13 via an amplifier 15 and a motion control board 28.

Figure 2:
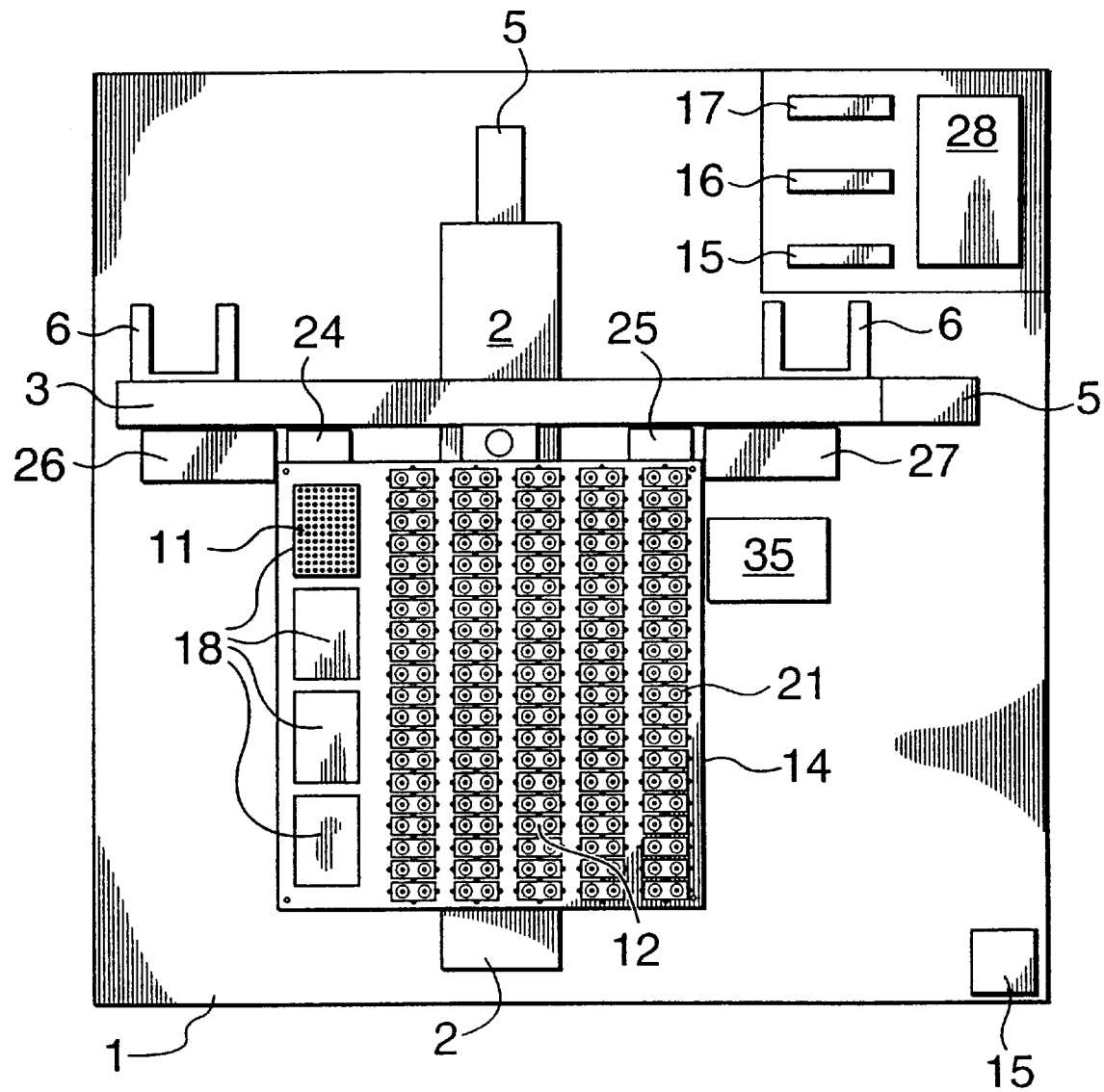
FIG. 2 is a top view of the apparatus of FIG. 1.

The platform 14 is designed to hold detachable sample reservoirs 11 in predetermined positions 18. As shown in FIG. 2, a sample reservoir 11 is 96-well microtiter plates. The platform 14 also holds a series of substrates 12, which substrates are held in place by means of suction, created by drawing a vacuum through the holes 21 on the platform underneath the substrate.

As seen in FIGS. 1 and 2, at opposite sides of the table 1 are vertical risers 6, having upper ends that carry a second horizontal linear guide 3 mounted substantially transversely, above and straddling the platform 14 and the first linear guide 2.

The second horizontal linear guide 3 carries a computer controlled motor 5b connected to a drive mechanism (not shown) such as a lead screw which is in threaded engagement with a carriage (not shown) which can be moved along the guide 3 by operation of the motor 5b, linked to the computer 13 via an amplifier 16 and the motion control board 28.

A third linear guide 4 is attached to the second linear guide 3 by means of the carriage such that the third linear guide 4 is substantially perpendicular to the first linear guide 2 and the second linear guide 3. By means of the computer controlled motor 5b, the third linear guide 4 can be moved back and forth by the carriage along the axis of the second linear guide 3. A drive mechanism within the third linear guide 4, e.g. a lead screw that is meshed with the carriage, enables the third linear guide 4 to be moved vertically by a further computer controlled motor 5c and positioned in any desired vertical location within the range of movement. Computer control is achieved by connection of motor 5a to an amplifier 17 which is connected to the motion control board 28. Use of linear guide 2, linear guide 3, linear guide 4 and the three carriages, thus provides for motion in three dimensions.

Figure 3:
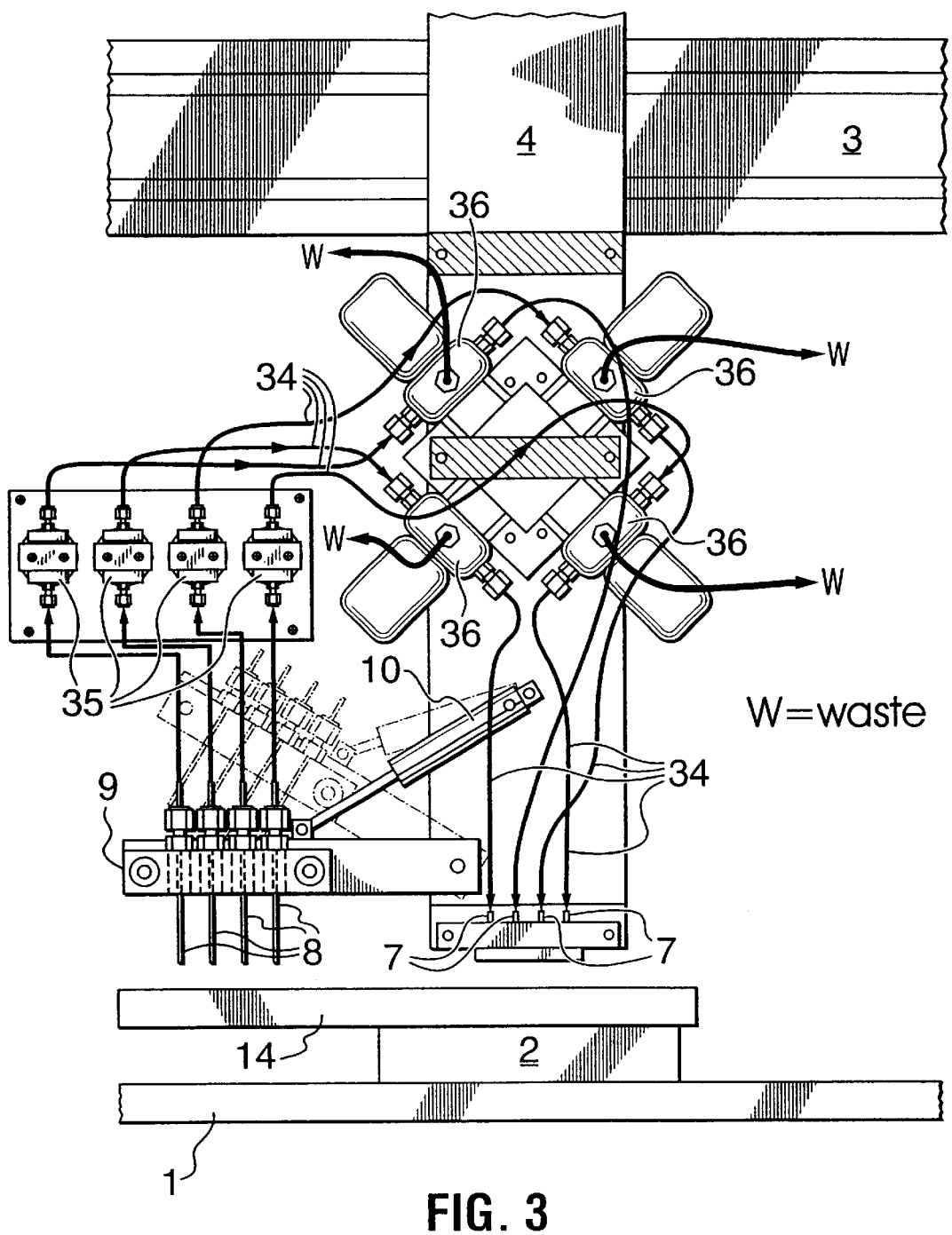
FIG. 3 is a somewhat schematic front view of the apparatus of FIG. 2.

As shown in FIG. 3, near the lower end of the third linear guide 4 is attached a sampling manifold 9 which contains four sampling needles 8 spaced linearly along the manifold at intervals to allow for simultaneous sample pick-up by all four sampling needles 8 from four sample locations in sample reservoirs 11. The sampling manifold 9 can be moved between two positions by activation of a pneumatic cylinder 10 connected between the sampling manifold 9 and third linear guide 4. As shown in FIG. 3 in solid lines the sampling manifold 9 is in the "down" position, for sampling (and cleaning). When the third linear guide 4 is being re-positioned the sampling manifold is pivoted to the "up" position as shown by the broken lines.

The base of the third linear guide 4 has piezoelectric inkjets 7 mounted thereon, the sampling needles 8 being connected to the piezoelectric inkjets 7 by microline tubing conduits 34 (FIG. 3). Each sampling needle 8 is connected through a conduit 34 to a micropump 35 and thence to a microvalve 36. Each microvalve 36 is adjustable so that the fluid delivered from the pump 35 can be directed selectively to the corresponding piezoelectric inkjet 7 or to the waste.

Figure 4A:
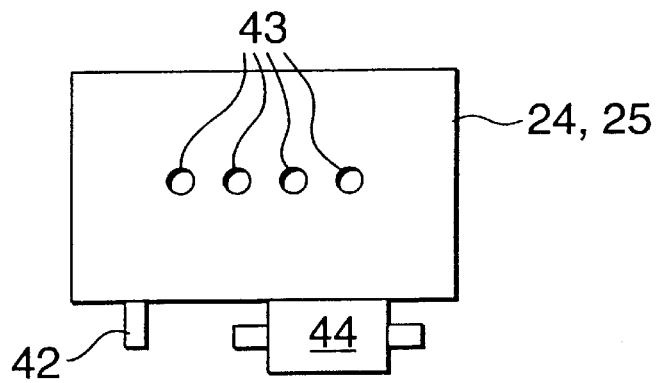
FIGS. 4a and 4b are schematic top and side views respectively of a solvent reservoir component of the apparatus.
Figure 4B:
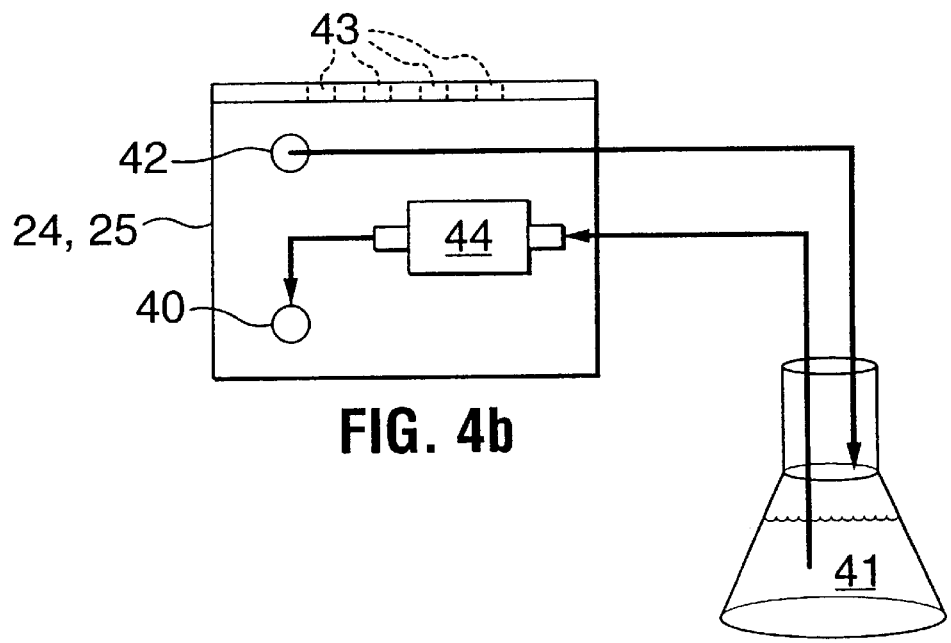

As shown in FIG. 2, also on the vibration isolation table 1 are two gravity overflow reservoirs 24, 25, positioned on opposite sides of the first linear guide 2 at the rear of the platform. The reservoirs 24, 25 contain cleaning solutions that can, when desired, be pumped through the interior of the apparatus. As shown in FIG. 4b, such overflow reservoirs 24, 25 are provided with a fluid in-feed aperture 40 in the lower portion of the overflow reservoir, into which is pumped the solution of interest from a fluid reservoir 41, through a pump 44. In the upper portion of the overflow reservoir is a fluid overflow aperture 42, out of which the liquid in the overflow reservoir returns to the fluid reservoir 41. The overflow reservoir is further provided with openings 43 on the top to allow for insertion of the sampling needles 8.

Figure 5:
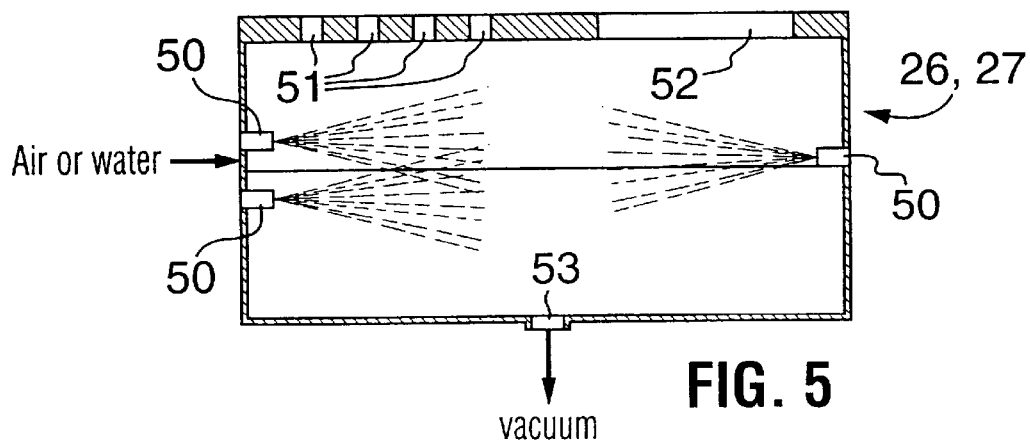
FIG. 5 is cross-sectional view of a wash station portion of the apparatus.

Also mounted to the vibration isolation table 1 are two cleaning boxes 26, 27 (FIG. 2) positioned on opposite sides of the first linear guide 2 outwardly of the gravity overflow reservoirs 24, 25. As shown in FIG. 5 the top of each box is provided with openings 51, 52 to accommodate the sampling needles 8 and the piezoelectric inkjets 7, respectively. Each box 26, 27 is provided with nozzles 50 on the interior sides thereof for the delivery of wash fluid from a wash fluid reservoir (not shown) onto the exterior surfaces of the sampling needles 8 and the piezoelectric inkjets 7. The lower part of the boxes are provided with an exit port 53 through which the waste wash fluid is sucked off into a vacuum trap.

In operation, a number of substrates 12 are placed on the platform 14 and selected samples are loaded into the sample reservoirs 11. The platform 14 mounted on the first linear guide 2 is moved into position such that the sampling manifold 9 is in position for sampling. The sampling manifold 9 is lowered by actuation of the pneumatic cylinder 10, and the third linear guide 4 is lowered, to place the sampling needles 8 into the sample reservoirs 11. The quantities of sample to be placed on the microarray are taken up through the sampling needles 8 by way of the micropumps 35 and delivered through the conduits 34 to the piezoelectric inkjets 7, and the sampling manifold 9 retracted. The piezoelectric inkjets 7 are positioned over the substrate 12 and the piezoelectric inkjets 7 deliver the samples onto the substrate 12. This process is repeated such that multiple samples are delivered to the selected substrates 12 at predetermined locations to form a microarray.

To prevent cross-contamination of samples, the sampling needles 8, the conduit 34, the micropump 35, the microvalves 36, and the piezoelectric inkjets 7 are cleaned between take-up of different samples. This is done using the two gravity overflow reservoirs, one 24 containing saline and the other 25 containing water. Saline or water is taken up by sampling needle 8 and delivered through the conduit 34 to the piezoelectric inkjets 7 to flush the system. Following this the cleaning boxes 26, 27, are used to spray water and/or air on the exterior surfaces of the sampling needles 8 and the piezoelectric inkjets 7.

The whole of the process may be automated. Motion control, digital actuation, sample processing, and micropumping can all be controlled by means of computer using specialized computer programs designed therefor. Certain functions such as the recirculation of fluid through the gravity overflow reservoirs can be run continuously during operation and do not require computer control.

A variety of liquid reagents can be dispensed using the described apparatus. For example, the liquids may contain DNA, RNA, modified nucleic acids and nucleic acid analogues, peptides, antibodies, antigens, enzymes, and cells. The apparatus can also dispense activator or inhibitor fluids. An activator fluid is one which makes possible coupling to the substrate, or causes a synthesis reaction with a previously deposited reagent. An inhibitor fluid protects an area on the substrate to prevent the material in the area from reacting.

Piezoelectric inkjets 7 preferred are drop-on-demand printer heads which are able to deliver small metered amounts of liquids quickly and accurately. The amount of material delivered will depend on the specific use, and may be for example 10 to 1000 picolitres (pl), preferably 20 to 100 pl, and most preferred 35 pl.

Examples of sample reservoirs include 96-well and 384-well microtiter plates, Eppendorf™ tubes, and the like.

Examples of sampling devices include sampling needles, which may be made of stainless steel bore tubing and may include syringe tips.

In other embodiments, the gravity overflow reservoirs and the cleaning boxes may be located in any suitable position.

The micropumps 35 may be activated intermittently or continuously. Intermittent activation may be achieved using an AC→DC relay under the control of the motion control board.

Components of the apparatus may be provided separately for assembly, together with instructions for assembly and use of the apparatus.

Numerous modifications, variations, and adaptations may be made to the particular embodiments of the invention described above without departing from the scope of the invention which is defined in the claims.

I claim:

1. A method for forming a microarray of biological materials on a substrate, comprising:

providing a plurality of sample reservoirs which contain samples;

providing a sampling device;

positioning the sampling device adjacent to the sample reservoirs;

using the sampling device to draw a selected sample into the sampling device from the sample reservoirs;

delivering the selected sample to an ejector through a conduit;

providing a substrate;

positioning the ejector adjacent to the substrate using a transport mechanism for moving both the substrate-holding support and the ejector relative toward each other;

delivering the sample from the ejector to a predetermined location on the substrate;

repeating the above steps after cleaning the sampling device the conduit and the ejector such that multiple samples are delivered to the substrate at predetermined locations to form a microarray of biological materials.

2. The method of claim 1 comprising cleaning the sampling device, the conduit, and the ejector.

3. The method of claim 2 comprising:

providing one or more solvent reservoirs;

positioning the sampling device in communication with solvent in said solvent reservoir;

drawing-up the solvent into said sampling device; and purging the inner portion of the sampling device, the conduit, and the ejector using said drawn-up solvent.

4. The method of claim 2, comprising: providing a wash station comprising one or more nozzles capable of dispensing wash liquid onto an exterior surface of the sampling device and/or ejector;

positioning the sampling device and/or ejector adjacent to said nozzle;

delivering wash liquid to exterior surface of the sampling device and/or ejector to effect washing.

5. The method of claim 2 comprising: providing a drying station comprising one or more drying nozzles capable of dispensing a gas onto an exterior surface of the sampling device and/or ejector;

positioning the sampling device and/or ejector adjacent to said drying nozzle;

delivering gas to exterior surface of the sampling device and/or ejector to effect drying.

6. The method of claim 5, wherein said gas is air.

* * * * *